United States Patent
Hyung et al.

(10) Patent No.: US 10,583,018 B2
(45) Date of Patent: Mar. 10, 2020

(54) METHOD OF IDENTIFYING PARAMETER OF CHARACTERISTIC OF MUSCLE, AND WALKING ASSISTANCE APPARATUSES AND METHOD BASED ON THE METHOD

(71) Applicant: Samsung Electronics Co., Ltd., Suwon-si, Gyeonggi-do (KR)

(72) Inventors: Seungyong Hyung, Yongin-si (KR); Youngjin Park, Seoul (KR); Youngbo Shim, Seoul (KR); Bokman Lim, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 285 days.

(21) Appl. No.: 15/468,444

(22) Filed: Mar. 24, 2017

(65) Prior Publication Data
US 2018/0078391 A1 Mar. 22, 2018

(30) Foreign Application Priority Data
Sep. 19, 2016 (KR) .................. 10-2016-0119200

(51) Int. Cl.
*A61F 2/72* (2006.01)
*A61B 5/00* (2006.01)
(Continued)

(52) U.S. Cl.
CPC .............. *A61F 2/72* (2013.01); *A61B 5/0488* (2013.01); *A61B 5/112* (2013.01); *A61B 5/4528* (2013.01); *A61B 5/4836* (2013.01); *A61F 2/60* (2013.01); *A61H 1/0244* (2013.01); *A61H 3/00* (2013.01); *A61B 5/224* (2013.01);
(Continued)

(58) Field of Classification Search
CPC .................. A61F 2/60; A61B 5/0488
See application file for complete search history.

(56) References Cited

U.S. PATENT DOCUMENTS

| 8,828,093 B1 | 9/2014 | Kuiken et al. |
| 2007/0293782 A1 | 12/2007 | Marino |
(Continued)

FOREIGN PATENT DOCUMENTS

| JP | 4384562 B | 10/2009 |
| KR | 10-1492478 B1 | 2/2015 |
| KR | 10-1603148 B1 | 3/2016 |
| KR | 2016/0023976 A | 3/2016 |
| KR | 2016/0023984 A | 3/2016 |

OTHER PUBLICATIONS

Christian Bauckhage et al., "Automatic detection of abnormal gait," Image and Vision Computing (2007), doi:10.1016/j.imavis.2006.10.004.
(Continued)

*Primary Examiner* — Yashita Sharma
(74) *Attorney, Agent, or Firm* — Harness, Dickey and Pierce, P.L.C.

(57) ABSTRACT

Disclosed is a method of identifying a parameter of a characteristic of a muscle, and walking assistance apparatuses and method based on the method. The method of identifying a parameter of a characteristic of a muscle includes estimating a first torque of a joint based on an electromyogram (EMG) signal, estimating a second torque of the joint based on motion data, and identifying a parameter of a characteristic of a muscle associated with the joint based on the first torque and the second torque.

11 Claims, 10 Drawing Sheets

(51) Int. Cl.
  *A61B 5/11* (2006.01)
  *A61B 5/0488* (2006.01)
  *A61H 1/02* (2006.01)
  *A61H 3/00* (2006.01)
  *A61F 2/60* (2006.01)
  *A61B 5/22* (2006.01)
  *A61F 2/70* (2006.01)

(52) U.S. Cl.
  CPC .. *A61F 2002/701* (2013.01); *A61H 2003/007* (2013.01); *A61H 2201/1207* (2013.01); *A61H 2201/1628* (2013.01); *A61H 2201/1652* (2013.01); *A61H 2201/5007* (2013.01); *A61H 2201/5061* (2013.01); *A61H 2201/5064* (2013.01); *A61H 2205/081* (2013.01); *A61H 2230/60* (2013.01); *A61H 2230/605* (2013.01); *A61H 2230/62* (2013.01)

(56) References Cited

U.S. PATENT DOCUMENTS

| | | |
|---|---|---|
| 2008/0170123 A1 | 7/2008 | Albertson |
| 2011/0213267 A1* | 9/2011 | Kakei .................. A61B 5/0488 600/546 |
| 2014/0159911 A1 | 6/2014 | Gray et al. |
| 2015/0332013 A1 | 11/2015 | Lee |

OTHER PUBLICATIONS

Hartmut Geyer et al. "A Muscle-Reflex Model that Encodes Principles of Legged Mechanics Produces Human Walking Dynamics and Muscle Activities," IEEE Transactions on Neural Systems and Rehabilitation Engineering, vol. X, No. X (2010), pp. 1-10.

* cited by examiner

METHOD OF IDENTIFYING PARAMETER OF CHARACTERISTIC OF MUSCLE, AND WALKING ASSISTANCE APPARATUSES AND METHOD BASED ON THE METHOD

CROSS-REFERENCE TO RELATED APPLICATION

This application claims under 35 U.S.C. § 119 to Korean Patent Application No. 10-2016-0119200, filed on Sep. 19, 2016, in the Korean Intellectual Property Office, the entire contents of which are incorporated herein by reference in their entirety.

BACKGROUND

1. Field

At least one example embodiment relates to a method of identifying a parameter of a characteristic of a muscle, walking assistance apparatuses and/or a walking assistance method based on the identification.

2. Description of the Related Art

With the onset of rapidly aging societies, many people may experience inconvenience and pain from joint problems. Development in a medical field has brought about a life extension and thus, a high quality of life based on a healthy life has been regarded as important. In this context, there has been provided services for assisting the elderly or patients with normal activities. For example, interest in motion assistance apparatuses enabling the elderly or patients with joint problems to walk with less effort, may increase.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and pedial frames disposed on feet of the users. The pelvic frames and femoral frames may be connected rotatably by hip joint portions, the femoral frames and sural frames may be connected rotatably by knee joint portions, and the sural frames and pedial frames may be connected rotatably by ankle joint portions.

However, due to various musculoskeletal and nerve conditions of human body, technology for cooperating with the human body without a damage of the human body is still insufficient and thus, continuous research on motion assistance apparatuses is required.

There has been a lot of effort for providing a personalized algorithm matching various body structures and musculoskeletal and nerve deteriorating conditions of individuals. To this end, a customizing algorithm of adjusting details may be applied for each person in general. However, personnel expenses and service costs may increase in such case. Thus, it is difficult to realize a product in a mass production type and also difficult to reduce a price of the product.

SUMMARY

Some example embodiments relate to a method of identifying a parameter associated with a characteristic of a muscle.

In some example embodiment, the method may include estimating a first torque of a joint of a user based on an electromyogram (EMG) signal of a muscle associated with the joint; estimating a second torque of the joint based on motion data; and identifying a parameter of a characteristic of the muscle associated with the joint based on the first torque and the second torque.

In some example embodiments, the muscle includes at least one of a soleus muscle, a tibialis anterio muscle, a gastrocnemius muscle, a vastus lateralis muscle, a hamstring muscle, a gluteus maximus muscle, and a hip flexor muscle.

In some example embodiments, the parameter includes at least one of a muscular strength, an optimal length, a slack length, and a moving velocity of the muscle.

In some example embodiments, the identifying includes: updating an initial version of the parameter of the muscle based on a difference between the first torque and the second torque to generate an updated parameter; and repetitively estimating the first torque using the updated parameter.

In some example embodiments, the estimating of the first torque includes estimating the first torque by applying the EMG signal to muscle dynamics, and the estimating of the second torque includes estimating the second torque by applying the motion data to body dynamics.

Some example embodiments relate to a walking assistance method.

In some example embodiments, the walking assistance method includes identifying a parameter of a characteristic of a muscle associated with a joint based on a first torque of the joint and a second torque of the joint, the first torque being estimated based on an electromyogram (EMG) signal and the second torque being estimated based on motion data; and controlling a walking assistance apparatus based on a gait type determined using the parameter.

In some example embodiments, the controlling includes: diagnosing a gait-related disease corresponding to the characteristic of the muscle based on the identified parameter; and controlling the walking assistance apparatus based on the gait type corresponding to the gait-related disease.

In some example embodiments, the controlling includes: controlling the walking assistance apparatus based on the gait type selected from among a plurality of abnormal gait types based on the parameter.

In some example embodiments, the muscle includes at least one of a soleus muscle, a tibialis anterio muscle, a gastrocnemius muscle, a vastus lateralis muscle, a hamstring muscle, a gluteus maximus muscle, and a hip flexor muscle.

In some example embodiments, the parameter includes at least one of a muscular strength, an optimal length, a slack length, and a moving velocity of the muscle.

In some example embodiments, the identifying includes: updating an initial parameter of the muscle based on a difference between the first torque and the second torque to generate an updated parameter; and extracting the parameter of the muscle by repetitively estimating the first torque using the updated parameter.

In some example embodiments, the identifying includes: estimating the first torque by applying the EMG signal to muscle dynamics; estimating the second torque by applying the motion data to body dynamics; and identifying the parameter of the characteristic of the muscle associated with the joint using the first torque and the second torque.

Some example embodiments relate to an apparatus configured to identify a parameter.

In some example embodiments, the apparatus includes an interface configured to acquire an electromyogram (EMG) signal and motion data; and a controller configured to, estimate a first torque of a joint based on the EMG signal, estimate a second torque of the joint based on the motion data, and identify the parameter of a characteristic of a muscle associated with the joint based on the first torque and the second torque.

In some example embodiments, the muscle includes at least one of a soleus muscle, a tibialis anterio muscle, a gastrocnemius muscle, a vastus lateralis muscle, a hamstring muscle, a gluteus maximus muscle, and a hip flexor muscle.

In some example embodiments, the parameter includes at least one of a muscular strength, an optimal length, a slack length, and a moving velocity of the muscle.

In some example embodiments, the controller is configured to, update an initial parameter of the muscle based on a difference between the first torque and the second torque to generate an updated parameter, and extract the parameter of the muscle by repetitively estimating the first torque using the updated parameter.

In some example embodiments, the controller is configured to, estimate the first torque by applying the EMG signal to muscle dynamics, and estimate the second torque by applying the motion data to body dynamics.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
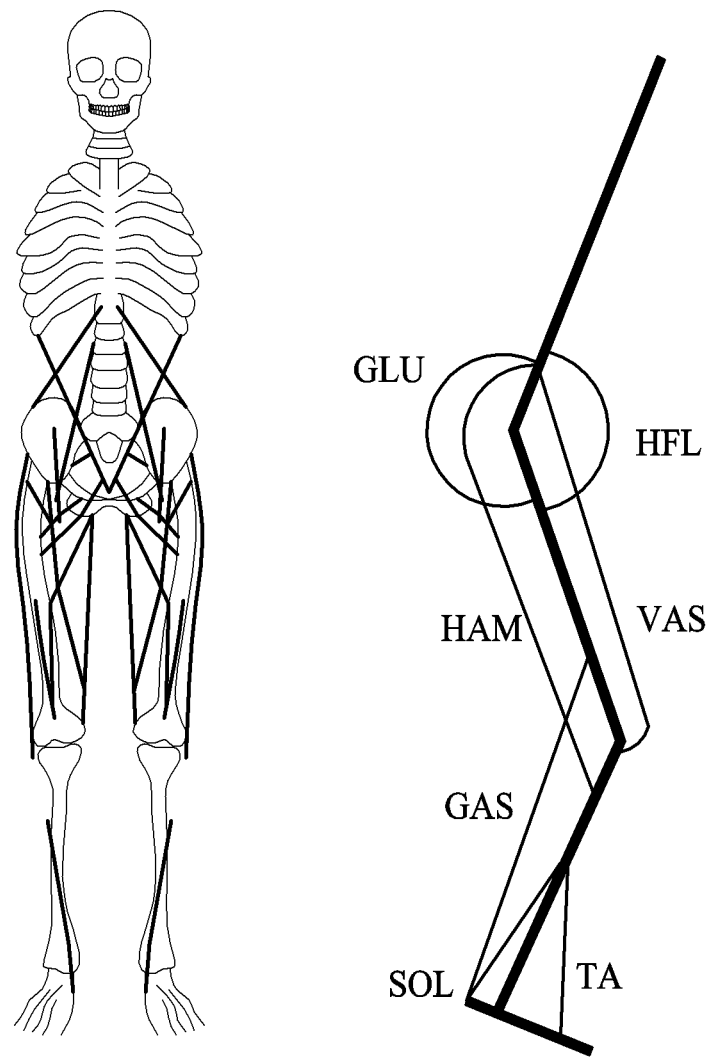
FIG. 1 illustrates an example of a musculoskeletal model for identifying a parameter of a characteristic of a muscle according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2A:
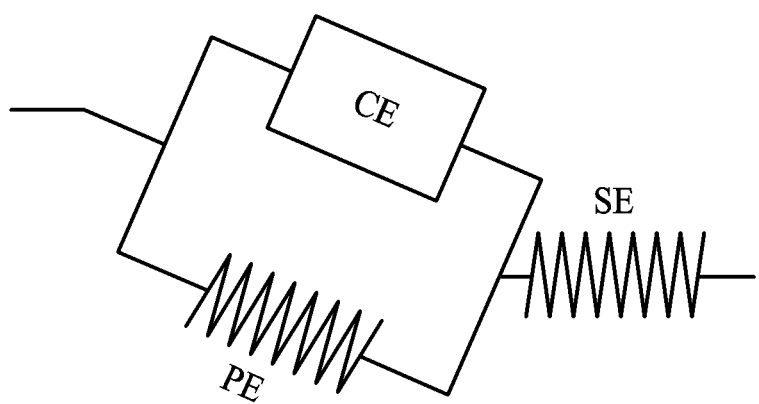
FIG. 2A illustrates an example of a heel-type muscle model according to at least one example embodiment.
Figure 2B:
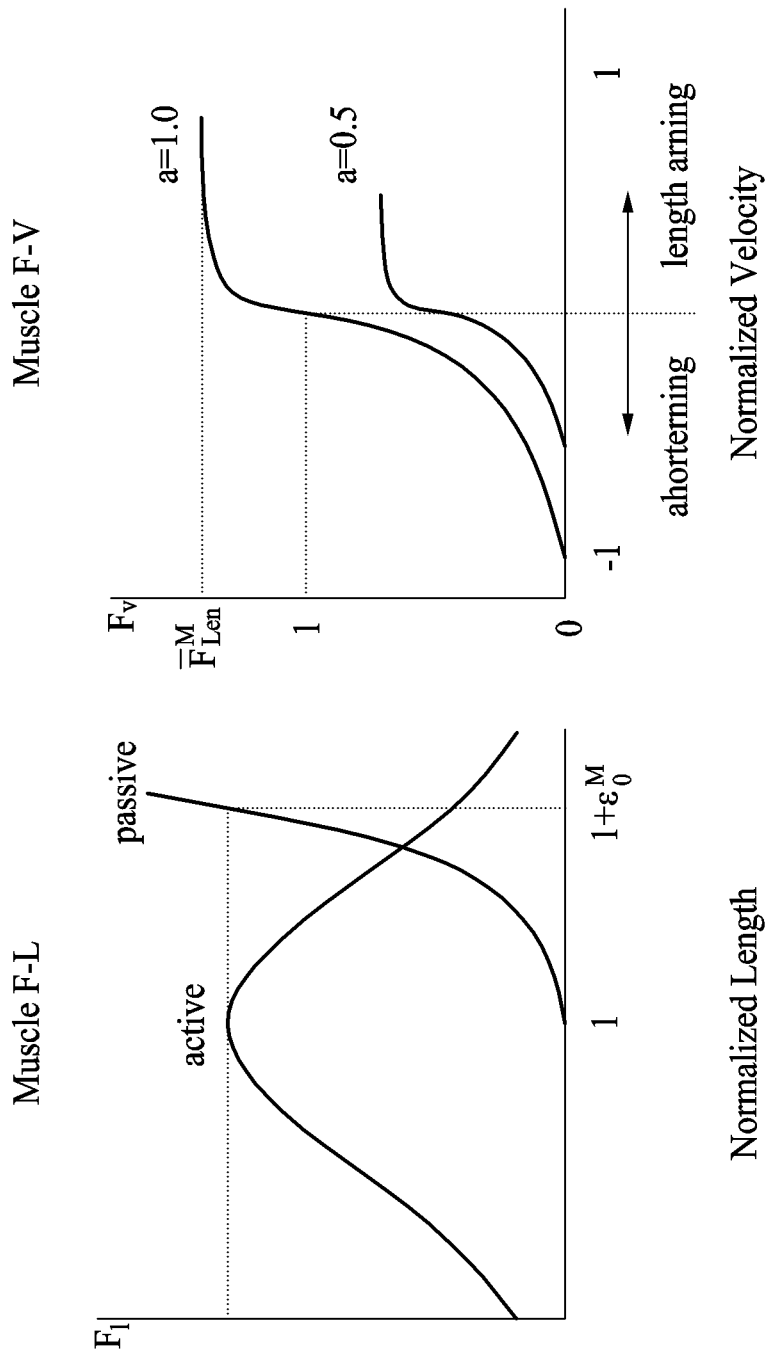
FIG. 2B illustrates an example of characteristics associated with a length and a speed of the heel-type muscle model of FIG. 2A.

FIG. 1 illustrates an example of a musculoskeletal model for identifying a parameter of a characteristic of a muscle according to at least one example embodiment, FIG. 2A illustrates an example of a heel-type muscle model according to at least one example embodiment, and FIG. 2B illustrates an example of characteristics associated with a length and a speed of the heel-type muscle model of FIG. 2A.

Referring to FIGS. 1 through 2B, for each and brevity of description, a musculoskeletal model including seven muscles may be used in an example of FIG. 1, and a heel-type muscle model may be used in an example of FIGS. 2A and 2B. However, the present disclosure is not limited thereto. A musculoskeletal model including at least N muscles, N being a natural number greater than or equal to 1, and various types of muscle models are also applicable based on an example.

A human gait may be structuralized to be a gait of a musculoskeletal model corresponding to a human body. The musculoskeletal model may be configured in a human body model including frames having desired (or, alternatively, predetermined) mass and inertia moment. The frames may configure parts of a head, a chest, a pelvis, a thigh, a calf, and a foot. Further, a joint may be formed in each portion connecting the frames. A muscle corresponding to a driving force may be formed between joints. The muscle may include at least one of a soleus muscle SOL, a tibialis anterio muscle TA, a gastrocnemius muscle GAS, a vastus lateralis muscle VAS, a hamstring muscle HAM, a gluteus maximus muscle GLU, or a hip flexor muscle HFL.

A muscle model corresponding to the muscle may be a heel-type model of FIG. 2A. The heel-type muscle model may include a serial element SE, a parallel element PE, and a contractile element CE corresponding to a muscle tendon unit.

A force generated in the contractile element CE may be expressed by Equation 1.

$$F_{ce} = AF_{max}F_l(l_{ce})F_v(V_{ce})$$ [Equation 1]

In Equation 1, A denotes an excitation signal, and $F_{max}$ denotes a maximal muscular strength. As illustrated in FIG. 2B, $F_l$ and $F_v$ respectively denote muscular strengths relative to a length and a velocity of a muscle of the contractile element CE, for example, a CE muscle. For example, $F_l$ corresponding to a value of the muscular strength relative to the length of the CE muscle is represented by a muscle F-L graph in a left portion of FIG. 2B, and $F_v$ corresponding to a value of the muscular strength relative to the velocity of the CE muscle is represented by a muscle F-V graph in a right portion of FIG. 2B. $l_{ce}$ and $V_{ce}$ denote the length and the velocity of the CE muscle, respectively.

As shown by Equation 1, a micro-excitation signal A occurring in a nervous system may be required to generate a force in the muscle. The excitation signal A may be, for example, an electromyogram (EMG) signal. The excitation signal A may trigger a positive feedback to be applied to the muscle. Through this, the force may be generated in the muscle.

A gait may be performed based on a general muscular strength of a user. Also, the gait may be performed to secure a stability with minimal energy consumption. A characteristic of a muscle may be used to predict a motion and/or a movement of the muscle, and thus, gait information may be acquired by identifying the characteristic of the muscle.

A parameter of the characteristic of the muscle may be extracted from power generated in the contractile element CE and used as a factor of determining the characteristic of the muscle. The parameter may include at least one of a muscular strength, an optimal length or an optimal muscular fiber length, a slack length, or a moving speed of the muscle. The motion and/or the movement of the muscle may be predicted through an identification of the parameter of the characteristic of the muscle.

For example, the parameter of the muscle may represent a human gait. By identifying the parameter of the muscle, information associated with a source of generating the human gait may be acquired in lieu of acquiring a gait as coordinates of a trajectory and a time at a domain corresponding to a superficial location. As such, by identifying a value of the parameter, a user or a gait of the user may be identified with increased accuracy.

As the foregoing, the human gait may be structured to be a gait of the musculoskeletal model, and a type of the gait may be represented through a parameter conversion of the characteristic of the muscle. For example, the gait may also be represented as a set of parameters associated with the characteristic of the muscle.

Figure 3:
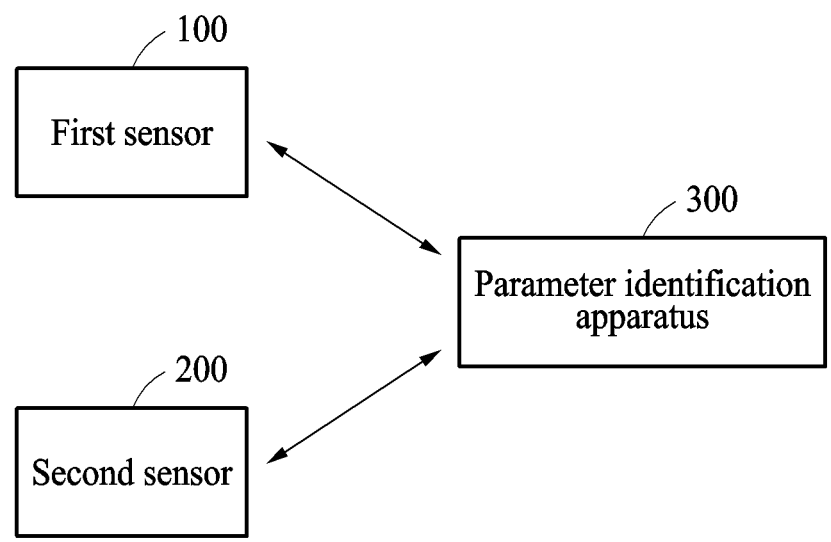
FIG. 3 is block diagram illustrating an example of a system including a parameter identification apparatus for identifying a parameter of a characteristic of a muscle according to at least one example embodiment.
Figure 4:
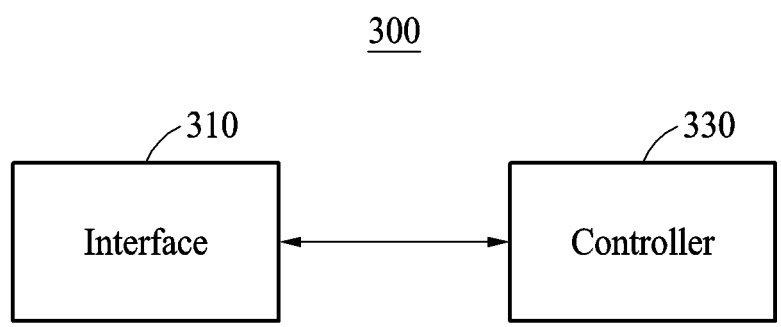
FIG. 4 is a block diagram illustrating the parameter identification apparatus of FIG. 3.

FIG. 3 is block diagram illustrating an example of a system including parameter identification apparatus for identifying a parameter of a characteristic of a muscle according to at least one example embodiment, and FIG. 4 is a block diagram illustrating the parameter identification apparatus of FIG. 3.

Referring to FIGS. 3 and 4, a system 10 may be a system for identifying a parameter of a characteristic of a muscle of human. The system 10 may include a first sensor 100, a second sensor 200, and a parameter identification apparatus 300.

The first sensor 100 may sense an EMG signal of a muscle of human. The first sensor 100 may be implemented as at least one EMG sensor. For example, an EMG sensor may be provided for each muscle of which an EMG signal is to be sensed. The first sensor 100 may transmit the EMG signal to the parameter identification apparatus 300.

The second sensor 200 may generate motion data of human. For example, the second sensor 200 may generate or measure motion data including information on a length and a position of a joint of human and information on a joint movement based on a gait. The second sensor 200 may be, for example, a motion capturing device and/or a force plate device. The second sensor 200 may transmit the motion data to the parameter identification apparatus 300.

Although FIG. 3 illustrates the first sensor 100 and the second sensor 200 disposed externally to the parameter identification apparatus 300 as an example, the disclosure is not limited thereto. Depending on an example, the first sensor 100 and the second sensor 200 may also be included in the parameter identification apparatus 300.

The parameter identification apparatus 300 may be an apparatus for identifying a parameter of a characteristic of a muscle.

For example, the muscle may include at least one of a soleus muscle, a tibialis anterio muscle, a gastrocnemius muscle, a vastus lateralis muscle, a hamstring muscle, a gluteus maximus muscle, or a hip flexor muscle. The parameter may include at least one of a muscular strength, an optimal length or an optimal muscular fiber length, a slack length, or a moving speed of the muscle.

Referring to FIG. 4, the parameter identification apparatus 300 may include an interface 310 and a controller 330.

The interface 310 may include a transmitting device having hardware and any necessary software for transmitting signals including, for example, data signals and control signals, and a receiving device having hardware and any necessary software for receiving signals including, for example, data signals and control signals.

The interface 310 may acquire or receive an EMG signal and motion data. For example, the interface 310 may acquire the EMG signal from the first sensor 100. Also, the interface 310 may acquire the motion data from the second sensor 200. The interface 310 may transmit the acquired EMG signal and motion data to the controller 330.

The controller 330 may include any device capable of processing data including, for example, an application application-specific integrated circuit (ASIC) configured to carry out specific operations based on input data, or a microprocessor configured as a special purpose processor by executing instructions included in computer readable code. The computer readable code may be stored on, for example, a memory (not shown). As discussed in more detail below with reference to FIG. 5, the computer readable code may configure the controller 330 to identify a parameter of a characteristic of the muscle associated with a joint based on a first torque and a second torque.

The controller 330 may estimate a torque of a joint associated or connected with a muscle based on the EMG signal and the motion data.

The controller 330 may estimate or calculate the first torque of a joint based on the EMG signal. The joint may indicate a joint associated or connected with the muscle. For example, the controller 330 may estimate the first torque by applying the EMG signal to muscle dynamics.

In one example, the controller 330 may estimate the first torque by substituting the EMG signal in Equation 1. In another example, the controller 330 may estimate the first torque by performing dynamic simulation using the musculoskeletal model of FIG. 1 in response to the EMG signal. In the dynamic simulation, the EMG signal may be an activation signal or an excitation signal activating a muscle of the musculoskeletal model or an activation signal.

The controller 330 may estimate the second torque of the joint based on the motion data. For example, the controller 330 may estimate the second torque by applying the motion data to body dynamics.

The controller 330 may identify the parameter of the characteristic of the muscle associated or connected with the joint based on the first torque and the second torque. For example, the controller 330 may repetitively estimate the first torque by adjusting the parameter through an optimizing process based on a difference between the first torque and the second torque. In this example, the controller 330 may extract an optimal parameter by performing the optimizing process to reduce (or, alternatively, minimize) the difference based on a variation in difference relative to a variation in parameter.

Figure 5:
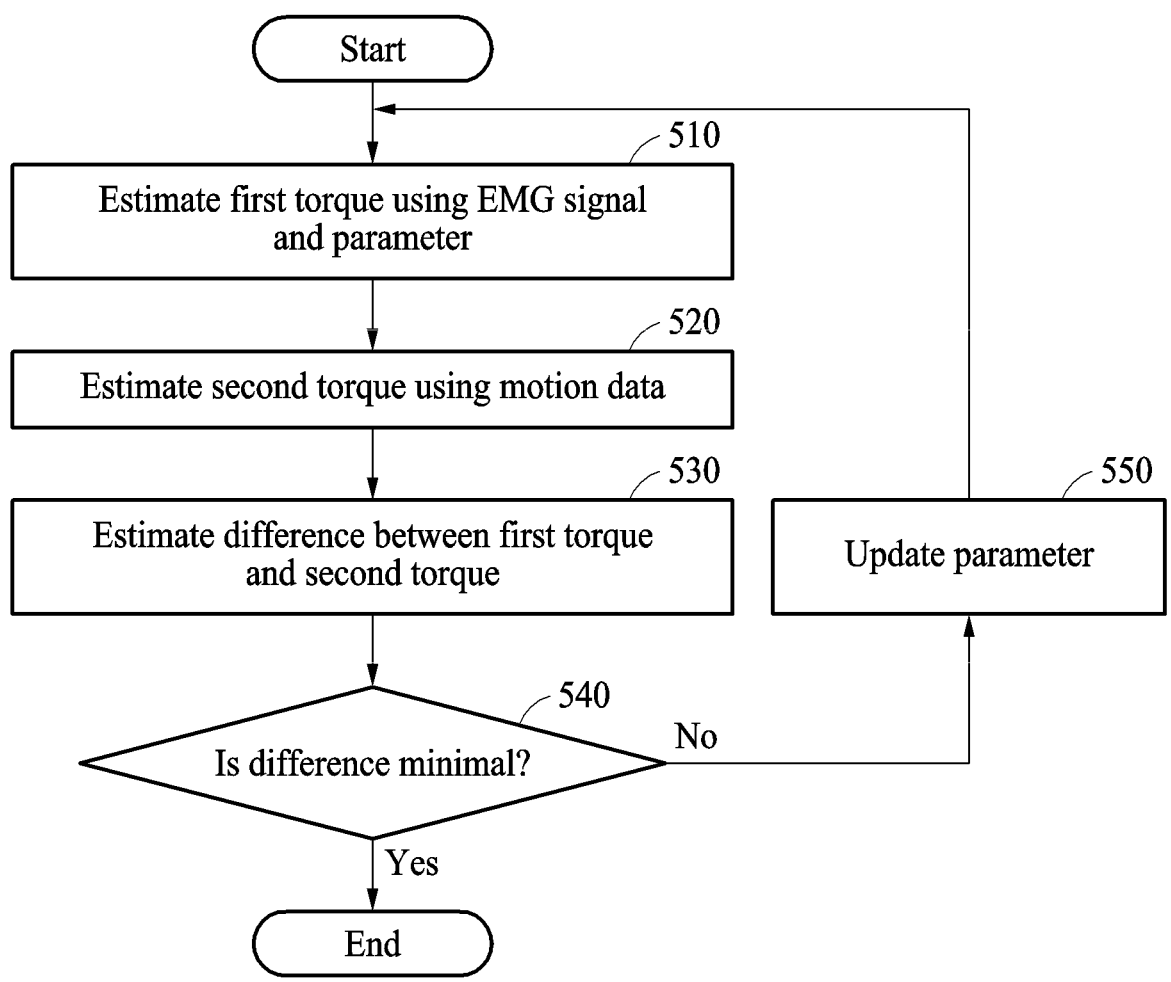
FIG. 5 is a flowchart illustrating an operation of the parameter identification apparatus of FIG. 3.

FIG. 5 is a flowchart illustrating an operation of the parameter identification apparatus of FIG. 3.

Referring to FIG. 5, in operation 510, the controller 330 may estimate a first torque by applying, to muscle dynamics, an EMG signal and a parameter of a characteristic of a muscle which is set initially.

In operation 520, the controller 330 may estimate a second torque by applying motion data to body dynamics.

In operation 530, the controller 330 may extract or calculate a difference between the first torque and the second torque. In operation 540, the controller 330 may verify whether the difference is a reduced (or, alternatively, a minimal) value.

In operation 550, when the difference is not the reduced (or, alternatively, the minimal) value, the controller 330 may update the parameter. The controller 330 may perform operations 510 through 540 using the updated parameter. The controller 330 may repetitively perform operations 510 through 550 until the difference is minimized.

The controller 330 may extract the parameter used when the difference is minimized, to be the optimal parameter of the characteristic of the muscle. The parameter may include at least one of a muscular strength, an optimal length or an optimal muscular fiber length, a slack length, or a moving speed of the muscle.

In this example, a time when the difference is reduced (or, alternatively, minimized) may indicate a state in which a change in difference is absent in a process of repetitively performing operations 510 through 550, that is, a state in which a variation in difference is reduced (or, alternatively, minimized).

As described with reference to FIGS. 1 through 5, the parameter identification apparatus 300 may parameterize situations associated with a muscle and a gait nerve of a user based on an EMG signal and gait data, for example, motion data, and acquire a condition and a gait state of the user. Through this, a walking assistance apparatus may perform a customization with a minimal effort.

The foregoing example may be applicable to a method of diagnosing a human musculoskeletal disease, and applicable to a security and a method to provide a personalized Internet of things (IoT) service and perform a remote user identification as technology for identifying a user by acquiring gait feature of a user based on human gait data. Also, with an availability of remote recognition, the foregoing example may be applicable to a medical field to identify users suffering from a disease through a gait identification for each user, track a gait using a gesture recognition-based video device without need to perform an invasive inspection, and identify a patient group to which a gait of a user belongs.

Hereinafter, a walking assistance apparatus using a parameter identified by the parameter identification apparatus 300 will be described.

Figure 6:
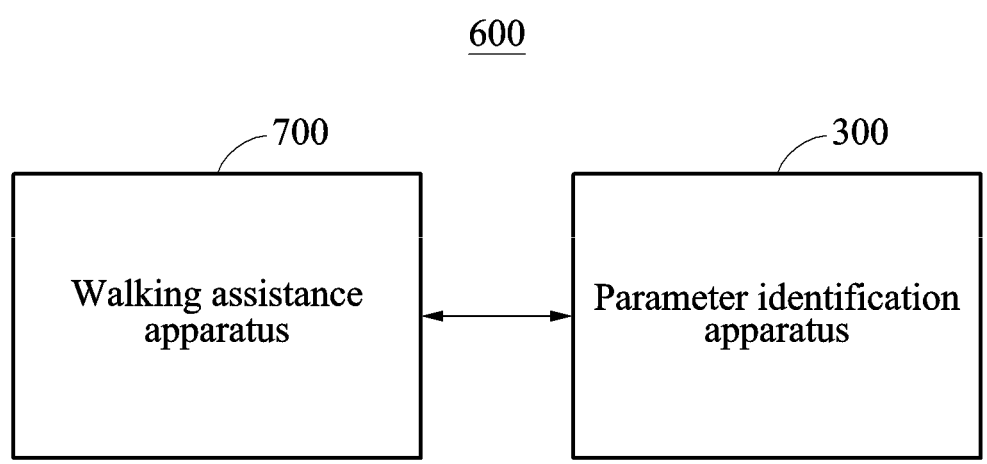
FIG. 6 is block diagram illustrating another example of a system including the parameter identification apparatus of FIG. 3.

FIG. 6 is block diagram illustrating another example of a system including the parameter identification apparatus of FIG. 3.

Referring to FIG. 6, a walking assistance system 600 may include a walking assistance apparatus 700 and a parameter identification apparatus 300. In this disclosure, the term "walking" may be interchangeably used as a term "gait".

The parameter identification apparatus 300 may identify a parameter of a characteristic of a muscle associated with a joint using a first torque of the joint estimated based on an EMG signal and a second torque of the joint estimated based on motion data. A configuration and an operation of the parameter identification apparatus 300 of FIG. 6 may be substantially the same as the configuration and operation of the parameter identification apparatus 300 described with reference to FIGS. 1 through 5 and thus, repeated descriptions will be omitted.

The parameter identification apparatus 300 may transmit the identified parameter to the walking assistance apparatus 700.

The walking assistance apparatus 700 may be worn by a target body, for example, a user, to assist the user during an exercise and/or walking. The target body may be, for example, a person, an animal, and a robot, however, an example of the target body is not limited thereto.

The walking assistance apparatus 700 may assist a gait and/or a motion of, for example, a hand, an upper arm, a lower arm, and the other part of an upper body of the user. Alternatively, the walking assistance apparatus 700 may assist a gait and/or a motion of, for example, a foot, a calf, a thigh, and the other part of a lower body of the user. Thus, the walking assistance apparatus 700 may assist a gait and/or a motion of a part of the user.

The walking assistance apparatus 700 may diagnose a gait-related disease corresponding to the characteristic of the muscle based on the identified parameter. Also, the walking assistance apparatus 700 may be controlled based on a gait type corresponding to the diagnosed gait-related disease. The gait-related disease may include, for example, a joint inflammation and a cerebral infarction.

Also, the walking assistance apparatus 700 may be controlled based on a gait type corresponding to the characteristic of the muscle among a plurality of abnormal gait types based on the identified parameter.

An abnormal gait may indicate a gait evolved to continue an abnormal or pathological gait pattern when a normal gait pattern collapses as a result of a functional disorder due to, for example, a partial damage, weakness, a loss of flexibility, a pain, a bad habit, and a neural or muscular injury. The abnormal gait may indicate, for example, a pathological gait pattern. In this disclosure, the term "abnormal" may be interchangeably used with the term "pathological".

In an example, the at least one abnormal gait type may include at least one of a crouch gait or genu recurvatum gait, a steppage gait or footdrop gait, an antalgic gait, an ataxic gait, a festinating gait, a vaulting gait, a lurching gait, an equinus gait, a short leg gait, a hemiplegic gait, a circumduction gait, a tabetic gait, a neurogenic gait, a scissoring gait, and a Parkinsonian gait. The lurching gait may indicate any form of staggering gait and include, for example, a waddling gait, a gluteus maximus gait, and a trendelenburg gait. The waddling gait may indicate a gait characterized in swaying from side to side. The gluteus maximus gait may indicate a gait in which a chest is bent backward to maintain a hip extension and a trunk movement is suddenly exaggerated to walk from time to time. The trendelenburg gait may indicate a gait performed by tilting a chest toward a weakened leg to maintain a center of gravity and prevent a pelvis of a weakened side from drooping when standing on the ground with a weakened lower limb.

The crouch gait may indicate a gait performed with a posture of hunching all joints of a hip, a knee, and an ankle to overcome a gait instability. The steppage gait may indicate a gait in which toes are bent downward to the ground and a top of a foot is dropped to the ground. The antalgic gait may indicate a gait for avoiding a pain on a painful portion. The ataxic gait may indicate a gait characterized by an unsteady stride, a wide space between feet, a shaken body, and an unstable step appearing intoxicated. The festinating gait may indicate a gait performed with stiff arms, a trunk flexed forward, a short stance, and accelerating steps as if unbreakable. The vaulting gait may indicate a gait using a leg of a non-affected side, for example, a non-paralyzed side, in lieu of a leg of an affected side, for example, a paralyzed side when a knee joint is not extendable. The equines gait may indicate a gait performed using tiptoes while heels are not in contact with the ground. The hemiplegic gait may indicate a gait in which, due to a stiffness, an entire body is slightly tilted to the affected side, a swing of an upper arm in the affected side is lost, a shoulder of the affected side is in a descending state, and the lower limb appears in a primitively curved form. The circumduction gait may indicate a gait in which an entire leg swings due to a difficulty in bending the knee. The scissoring gait may indicate a gait performed by crossing or grazing legs or knees against to one another with a squatting posture in a state in which the legs are slightly bent inward. The Parkinsonian gait may indicate a gait performed as if shuffling a sole on the ground with an anterior flexion posture.

Although FIG. 6 illustrates the parameter identification apparatus 300 disposed externally to the walking assistance apparatus 700 as an example, the disclosure is not limited thereto. Depending on an example, the parameter identification apparatus 300 may also be included in the walking assistance apparatus 700.

Figure 7:
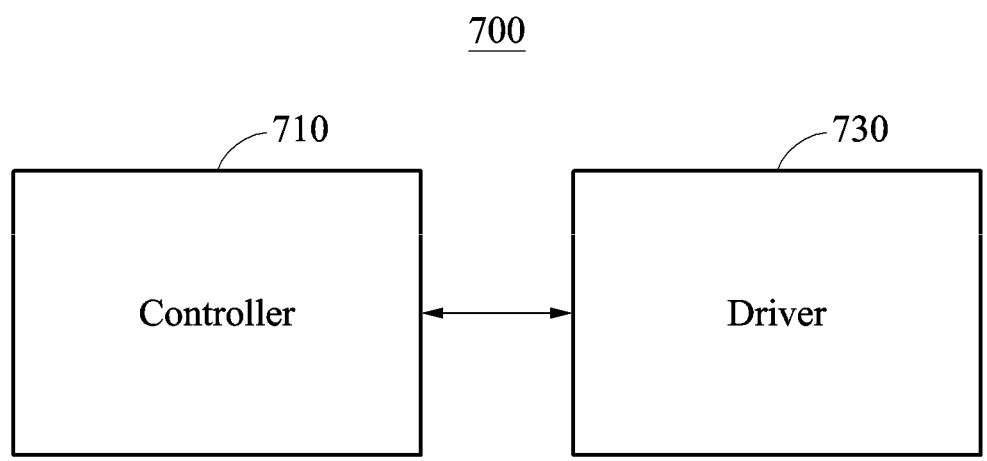
FIG. 7 is a block diagram illustrating a walking assistance apparatus of FIG. 6.
Figure 8:
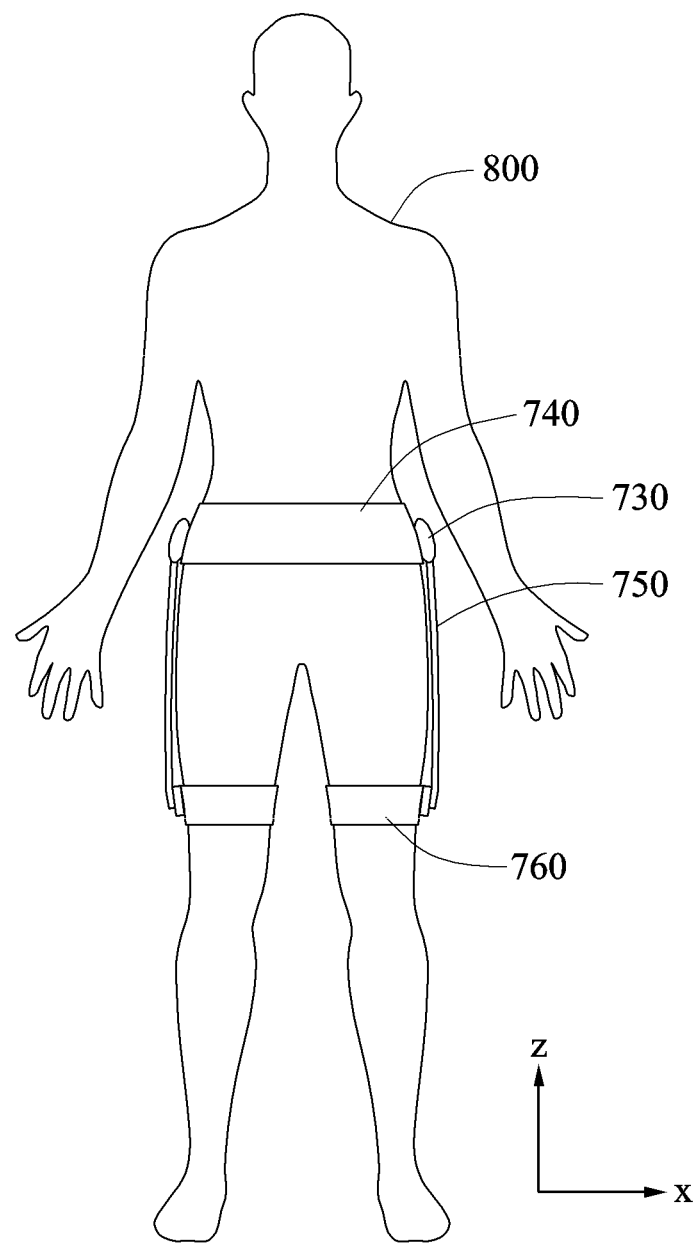
FIG. 8 is a front view of a target body wearing the walking assistance apparatus of FIG. 6.
Figure 9:
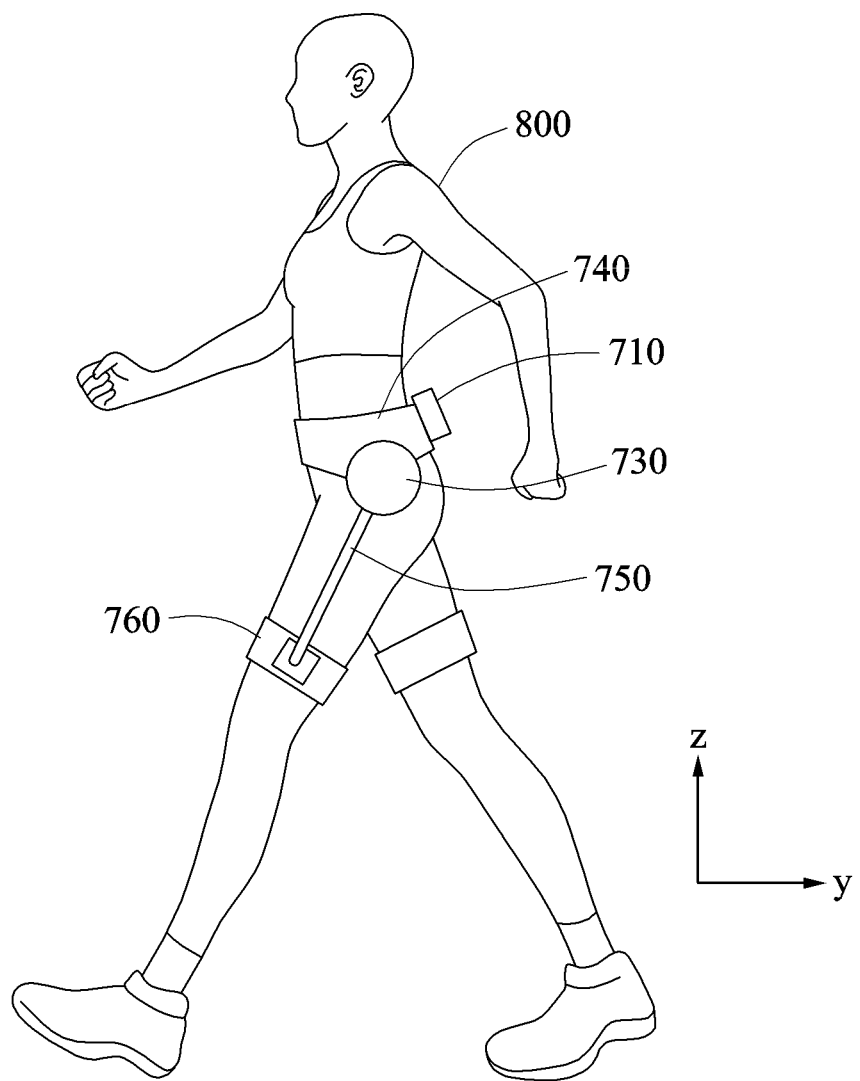
FIG. 9 is a side view of a target body wearing the walking assistance apparatus of FIG. 6.

FIG. 7 is a block diagram illustrating a walking assistance apparatus of FIG. 6, FIG. 8 is a front view of a target body wearing the walking assistance apparatus of FIG. 6, and FIG. 9 is a side view of a target body wearing the walking assistance apparatus of FIG. 6.

Referring to FIGS. 6 through 9, the walking assistance apparatus 700 may include a controller 710 and a driver 730. The walking assistance apparatus 700 may also include a fixing member 740, a force transmitting member 750, and a supporting member 760.

Although FIGS. 8 and 9 illustrate the walking assistance apparatus 700, for example, a hip-type walking assistance apparatus, operating on a thigh of a user 800, the type of the walking assistance apparatus 700 is not limited thereto. The walking assistance apparatus 700 may be applicable to, for example, a walking assistance apparatus that supports an entire pelvic limb, a walking assistance apparatus that supports a portion of a pelvic limb, and the like. The walking assistance apparatus that supports a portion of a pelvic limb may be applicable to, for example, a walking assistance apparatus that supports up to a knee, and a walking assistance apparatus that supports up to an ankle.

The controller 710 may include any device capable of processing data including, for example, an application application-specific integrated circuit (ASIC) configured to carry out specific operations based on input data, or a microprocessor configured as a special purpose processor by executing instructions included in computer readable code. The computer readable code may be stored on, for example, a memory (not shown). For example, the computer readable code may configure the controller 710 as a special purpose processor to receive an identification parameter from the parameter identification apparatus 300, where the identification parameter indicates at least one of a muscular strength, an optimal length, a slack length, and a moving velocity of a muscle, and to generate an assist torque profile based on a gait type corresponding to a characteristic of the muscle among a plurality of abnormal gait types based on the identified parameter.

The controller 710 may control an overall operation of the walking assistance apparatus 700. For example, the controller 710 may control the driver 730 to output a driving force to assist a gait of the user 800. The driving force may be, for example, an assistance torque.

The controller 710 may diagnose a gait-related disease corresponding to a characteristic of a muscle based on an identified parameter, and generate an assist torque profile based on a gait type corresponding to the diagnosed gait-related disease.

Also, the controller 710 may generate an assist torque profile based on a gait type corresponding to a characteristic of a muscle among a plurality of abnormal gait types based on an identified parameter.

The driver 730 may be disposed on one or more of a left hip portion and a right hip portion of the user 800 to drive one or more of the hip joints of the user 800. The driver 730 may generate a force to assist a gait of the user 800 based on the assist torque profile generated in the controller 710.

The fixing member 740 may be attached to a part, for example, a waist of the user 800. The fixing member 740 may be in contact with at least a portion of an external surface of the user 800. The fixing member 740 may cover along the external surface of the user 800.

The force transmitting member 750 may connect the driver 730 and the supporting member 760. The force transmitting member 750 may transmit the driving force received from the driver 730 to the supporting member 760. As an example, the force transmitting member 750 may be a longitudinal member such as, for example, a wire, a cable, a string, a rubber band, a spring, a belt, and a chain.

The supporting member 760 may support a target part, for example, a thigh of the user 800. The supporting member 760 may be disposed to cover at least a portion of the user 800. The supporting member 760 may exert a force on the target part of the user 800 using the driving force received from the force transmitting member 750.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of identifying a parameter associated with a characteristic of a muscle, the method comprising:
    estimating a first torque of a joint of a user based on an electromyogram (EMG) signal of a muscle associated with the joint;
    estimating a second torque of the joint based on motion data; and
    identifying a parameter of a characteristic of the muscle associated with the joint based on the first torque and the second torque.

2. The method of claim 1, wherein the muscle includes at least one of a soleus muscle, a tibialis anterio muscle, a gastrocnemius muscle, a vastus lateralis muscle, a hamstring muscle, a gluteus maximus muscle, and a hip flexor muscle.

3. The method of claim 1, wherein the parameter includes at least one of a muscular strength, an optimal length, a slack length, and a moving velocity of the muscle.

4. The method of claim 1, wherein the identifying comprises:
    updating an initial version of the parameter of the muscle based on a difference between the first torque and the second torque to generate an updated parameter; and
    repetitively estimating the first torque using the updated parameter.

5. The method of claim 1, wherein
    the estimating of the first torque includes estimating the first torque by applying the EMG signal to muscle dynamics, and
    the estimating of the second torque includes estimating the second torque by applying the motion data to body dynamics.

6. An apparatus configured to identify a parameter, the apparatus comprising:
    an interface configured to acquire an electromyogram (EMG) signal and motion data; and
    a controller configured to,
        estimate a first torque of a joint based on the EMG signal,
        estimate a second torque of the joint based on the motion data, and
        identify the parameter of a characteristic of a muscle associated with the joint based on the first torque and the second torque.

7. The apparatus of claim 6, wherein the muscle includes at least one of a soleus muscle, a tibialis anterio muscle, a gastrocnemius muscle, a vastus lateralis muscle, a hamstring muscle, a gluteus maximus muscle, and a hip flexor muscle.

8. The apparatus of claim 6, wherein the parameter includes at least one of a muscular strength, an optimal length, a slack length, and a moving velocity of the muscle.

9. The apparatus of claim 6, wherein the controller is configured to,
    update an initial parameter of the muscle based on a difference between the first torque and the second torque to generate an updated parameter, and
    extract the parameter of the muscle by repetitively estimating the first torque using the updated parameter.

10. The apparatus of claim 6, wherein the controller is configured to,
    estimate the first torque by applying the EMG signal to muscle dynamics, and estimate the second torque by applying the motion data to body dynamics.

11. A method of setting a walking assistance apparatus, the method comprising:

sensing an electromyogram (EMG) signal of a muscle associated with a joint of a user for estimating a first torque of the joint;

sensing motion data of the user for estimating a second torque of the joint of the user; and identifying a parameter of a characteristic of a muscle associated with joint of the user based on the first torque and the second torque.

\* \* \* \* \*